US00PP30602P2

(12) United States Plant Patent
Holtmaat

(10) Patent No.: US PP30,602 P2
(45) Date of Patent: Jun. 25, 2019

(54) *ANEMONE* PLANT NAMED 'ANEM081'

(50) Latin Name: *Anemone hupehensis*
Varietal Denomination: ANEM081

(71) Applicant: Henricus Maria Joseph Holtmaat, Zuidwolde (NL)

(72) Inventor: Henricus Maria Joseph Holtmaat, Zuidwolde (NL)

(73) Assignee: AB Kwekersrechten B.V., Zuidwolde (NL)

( * ) Notice: Subject to any disclaimer, the term of this patent is extended or adjusted under 35 U.S.C. 154(b) by 0 days.

(21) Appl. No.: 15/732,938

(22) Filed: Jan. 12, 2018

(51) Int. Cl.
*A01H 5/02* (2018.01)

(52) U.S. Cl.
USPC ..... Plt./263.1

(58) Field of Classification Search
USPC ..... Plt./263.1
See application file for complete search history.

*Primary Examiner* — Susan McCormick Ewoldt
(74) *Attorney, Agent, or Firm* — C. A. Whealy

(57) ABSTRACT

A new and distinct cultivar of *Anemone* plant named 'ANEM081', characterized by its upright and relatively compact plant habit; moderately vigorous to vigorous growth habit; early and freely flowering habit; long flowering period; single-type flowers that are red purple in color; and good garden performance.

2 Drawing Sheets

Botanical designation: *Anemone hupehensis*.
Cultivar denomination: 'ANEM081'.

BACKGROUND OF THE INVENTION

The present invention relates to a new and distinct cultivar of *Anemone*, botanically known as *Anemone hupehensis* and hereinafter referred to by the name 'ANEM081'.

The new *Anemone* plant is a product of a planned breeding program conducted by the Inventor in Zuidwolde, The Netherlands. The objective of the breeding program is to create new long-flowering *Anemone* plants with large attractive flowers.

The new *Anemone* plant originated from a cross-pollination made by the Inventor in September, 2015 in Zuidwolde, The Netherlands of two unidentified seedling selections of *Anemone hupehensis*, not patented. The new *Anemone* plant was discovered and selected by the Inventor as a single flowering plant within the progeny of the stated cross-pollination in a controlled greenhouse environment in Zuidwolde, The Netherlands in September, 2016.

Asexual reproduction of the new *Anemone* by in vitro meristem culture in a controlled environment in Zuidwolde, The Netherlands since November, 2017 has shown that the unique features of this new *Anemone* plant are stable and reproduced true to type in successive generations.

SUMMARY OF THE INVENTION

Plants of the new *Anemone* have not been observed under all possible combinations of environmental conditions and various cultural practices. The phenotype may vary somewhat with variations in environmental conditions such as temperature and light intensity without, however, any variance in genotype.

The following traits have been repeatedly observed and are determined to be the unique characteristics of 'ANEM081'. These characteristics in combination distinguish 'ANEM081' as a new and distinct *Anemone* plant:

1. Upright and relatively compact plant habit.
2. Moderately vigorous to vigorous growth habit.
3. Early and freely flowering habit.
4. Long flowering period.
5. Single-type flowers that are red purple in color.
6. Good garden performance.

Plants of the new *Anemone* can be compared to plants of the parent selections. Plants of the new *Anemone* differ primarily from plants of the parent selections in plant habit as plants of the new *Anemone* are more compact than plants of the parent selections.

Plants of the new *Anemone* can be compared to plants of *Anemone hupehensis* 'Pocahontas', disclosed in U.S. Plant Pat. No. 25,352. In side-by-side comparisons, plants of the new *Anemone* and 'Pocahontas' differ primarily in the following characteristics:

1. Plants of the new *Anemone* are more compact than plants of 'Pocahontas'.
2. Plants of the new *Anemone* and 'Pocahontas' differ in flower color as plants of 'Pocahontas' have light purple-colored flowers.

BRIEF DESCRIPTION OF THE PHOTOGRAPHS

The accompanying colored photographs illustrate the overall appearance of the new *Anemone* plant showing the colors as true as it is reasonably possible to obtain in colored reproductions of this type. Colors in the photographs may differ slightly from the color values cited in the detailed botanical description which accurately describe the colors of the new *Anemone* plant.

The photograph on the first sheet is a side perspective view of a typical plant of 'ANEM081' in a container.

The photograph at the top of the second sheet comprises a close-up view of typical leaves of 'ANEM081'.

The photograph at the bottom of the second sheet comprises a close-up view of a typical flower and flower buds of 'ANEM081'.

DETAILED BOTANICAL DESCRIPTION

The aforementioned photographs and following observations, measurements and values describe plants grown during the summer in 21-cm containers in an outdoor nursery in Zuidwolde, The Netherlands and under cultural practices typical of commercial *Anemone* production. During the production of the plants, day temperatures ranged from 18° C. to 30° C. and night temperatures ranged from 6° C. to 18° C. Plants were one year old when the photographs and description were taken. In the following description, color references are made to The Royal Horticultural Society Colour Chart, 2015 Edition, except where general terms of ordinary dictionary significance are used.

Botanical classification: *Anemone hupehensis* 'ANEM081'.

Parentage:

*Female, or seed, parent*.—Unidentified seedling selection of *Anemone hupehensis*, not patented.

*Male, or pollen, parent*.—Unidentified seedling selection of *Anemone hupehensis*, not patented.

Propagation:

*Type*.—In vitro meristem culture.

*Time to initiate roots, summer*.—About 14 days at temperatures about 25° C.

*Time to initiate roots, winter*.—About 20 days at temperatures about 10° C.

*Time to produce a rooted young plant, summer*.—About 60 days at temperatures about 20° C.

*Time to produce a rooted young plant, winter*.—About 75 days at temperatures about 18° C.

*Root description*.—Medium in thickness, fleshy; close to N199C to N199D in color, actual color of the roots is dependent on substrate composition, water quality, fertilizer type and formulation, substrate temperature and physiological age of roots.

*Rooting habit*.—Freely branching; dense.

Plant description:

*Plant and growth habit*.—Herbaceous perennial; upright and relatively compact plant habit with leaves developing from basal rosettes; numerous basal rosettes developing per plant; oblong in overall shape; moderately vigorous to vigorous growth habit; moderate growth rate.

*Plant height, soil level to top of foliar plane*.—About 22.2 cm.

*Plant height, soil level to top of floral plane*.—About 44.6 cm.

*Plant diameter*.—About 38.5 cm.

Leaf description:

*Arrangement, basal leaves*.—Alternate; simple.

*Arrangement, cauline leaves*.—Opposite; simple.

*Length, basal leaves*.—About 8.1 cm.

*Width, basal leaves*.—About 6.7 cm.

*Length, cauline leaves*.—About 5 cm.

*Width, cauline leaves*.—About 3.5 cm.

*Shape, basal leaves*.—Broadly ovate.

*Shape, cauline leaves*.—Ovate to broadly ovate.

*Apex, basal and cauline leaves*.—Acute.

*Base, basal leaves*.—Hastate.

*Base, cauline leaves*.—Attenuate.

*Margin, basal and cauline leaves*.—Serrulate; trilobed, depth of sinuses are medium to deep and divergent.

*Texture and luster, basal and cauline leaves, upper surface*.—Smooth, glabrous; matte.

*Texture and luster, basal and cauline leaves, lower surface*.—Sparsely pubescent; matte.

*Venation pattern, basal and cauline leaves*.—Laciniate.

*Color, basal and cauline leaves*.—Developing leaves, upper surface: Close to 143A. Developing leaves, lower surface: Close to 138B. Fully expanded leaves, upper surface: Close to NN137B venation, close to 144B. Fully expanded leaves, lower surface: Close to between 138B and 147B; venation, close to 144C.

*Leaf petioles*.—Length, basal leaves: About 13.7 cm. Length, cauline leaves: About 8 mm. Diameter, basal and cauline leaves: About 1.75 mm. Strength, basal and cauline leaves: Strong. Texture and luster, basal and cauline leaves, upper and lower surfaces: Sparsely pubescent; glossy. Color, basal and cauline leaves, upper and lower surfaces: Close to 144A.

*Stipules*.—Quantity and arrangement: Two, opposite at the base of each leaf. Length: About 1.2 cm. Diameter: About 3 mm. Shape: Narrowly oblong. Texture, upper surface: Smooth, glabrous. Texture, lower surface: Sparsely pubescent. Color, upper and lower surfaces: Close to 157A.

Flower description:

*Flower arrangement and flowering habit*.—Single-type rotate flowers arranged in simple and compound cymes; freely flowering habit with 150 flowers developing per plant; flowers face mostly upright to slightly outwardly.

*Fragrance*.—None detected.

*Natural flowering season*.—Plants of the new *Anemone* begin flowering about ten months after planting and flower during summer until the late summer in The Netherlands.

*Flower longevity*.—Individual flowers last about ten days on the plant; flowers not persistent.

*Inflorescence height*.—About 40.2 cm.

*Inflorescence diameter*.—About 13.3 cm.

*Flower diameter*.—About 5.8 cm.

*Flower length (depth)*.—About 1.8 cm.

*Flower buds*.—Length: About 1.2 cm. Diameter: About 9 mm. Shape: Ovate. Texture and luster: Densely pubescent; matte. Color: Close to N186C; towards the base, close to 145A to 145B.

*Petals*.—Absent.

*Sepals*.—Quantity and arrangement: Five in a single whorl. Length: About 2.6 cm to 3.3 cm. Width: About 2.3 cm to 2.7 cm. Shape: Ovate to obovate. Apex: Obtuse to broadly acute. Base: Cuneate. Margin: Entire. Texture and luster, upper surface: Smooth, glabrous; velvety; matte. Texture and luster, lower surface: Densely pubescent; slightly glossy. Color: When opening, upper surface: Close to 71A and 72B. When opening, lower surface: Close to 64A. Fully opened, upper surface: Close to 70B and 71A; venation, similar to lamina colors; color becoming closer to 70B and towards the base and apex, close to 64A to 64B with development. Fully opened, lower surface: Close to 70A and 70B; venation, similar to lamina color; color becoming closer to 64A and 64B with development.

*Peduncles*.—Length: About 29.2 cm. Diameter: About 2 mm. Aspect: About 10° from vertical. Strength: Strong. Texture and luster: Pubescent; somewhat glossy. Color: Close to 144A occasionally tinged with close to N200A.

*Pedicels*.—Length: About 11.5 cm. Diameter: About 1.5 mm. Aspect: About 30° from the peduncle axis. Strength: Moderately strong. Texture and luster:

Densely pubescent; slightly glossy. Color: Close to 148B occasionally tinged with close to N199A to N199B.

*Reproductive organs*.—Androecium: Stamen number per flower: About 150. Filament length: About 7 mm. Filament color: Close to 150D. Anther shape: Oblong. Anther length: About 1.75 mm. Anther diameter: About 0.5 mm. Anther color: Close to 14A. Amount of pollen: Moderate. Pollen color: Close to 11D. Gynoecium: Pistil number per flower: About 240. Pistil length: About 1 mm. Stigma shape: Club-shaped. Stigma length: About 0.5 mm. Stigma diameter: About 0.5 mm. Stigma color: Close to N144A. Style length: About 0.5 mm. Style color: Close to 150D. Ovary color: Close to 144A.

*Seeds and fruits*.—Seed and fruit development have not been observed on plants of the new *Anemone* to date.

Garden performance: Plants of the new *Anemone* have been observed to have good garden performance, to tolerate high temperatures of about 35° C. and to be suitable for USDA Hardiness Zones 4 through 9.

Pathogen & pest resistance: Plants of the new *Anemone* have not been observed to be resistant to pathogens and pests common to *Anemone* plants.

It is claimed:

1. A new and distinct *Anemone* plant named 'ANEM081' as illustrated and described.

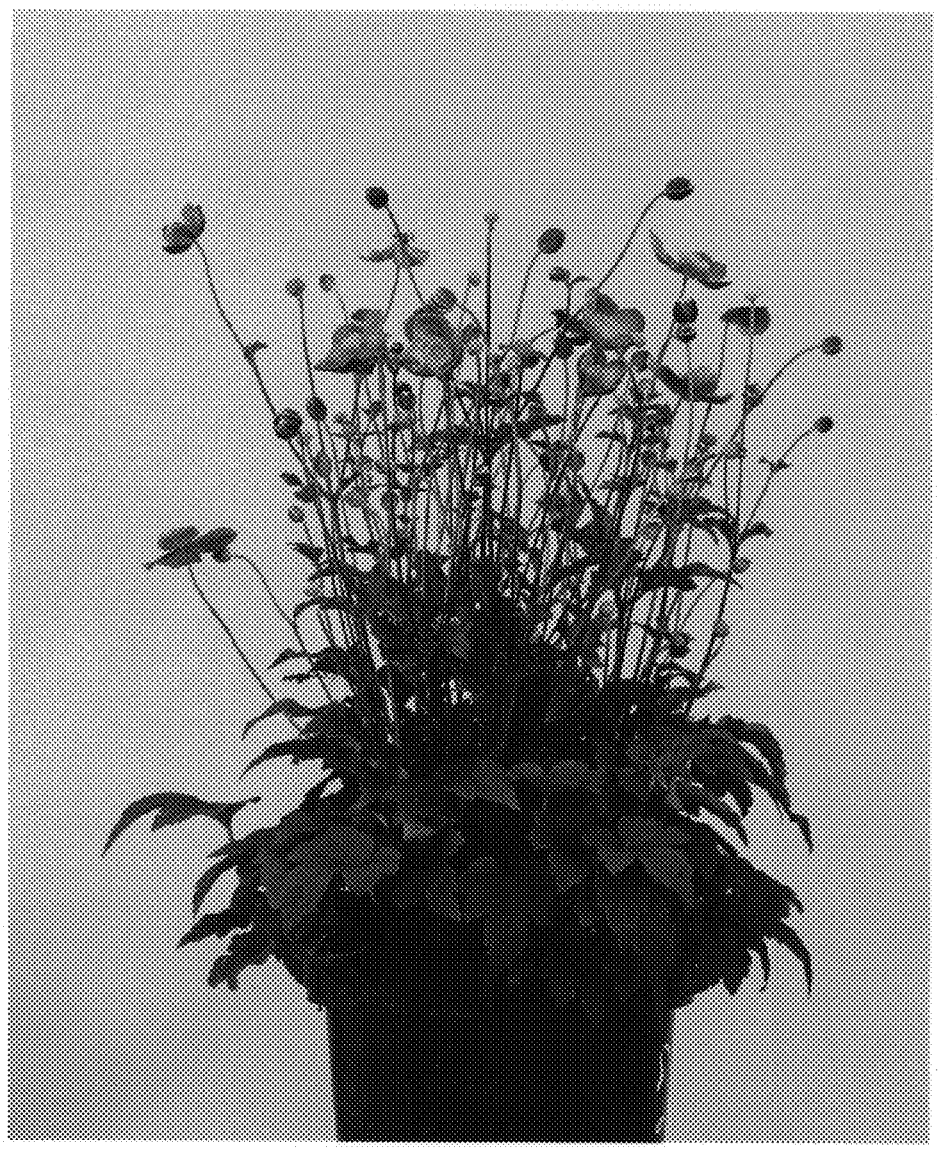

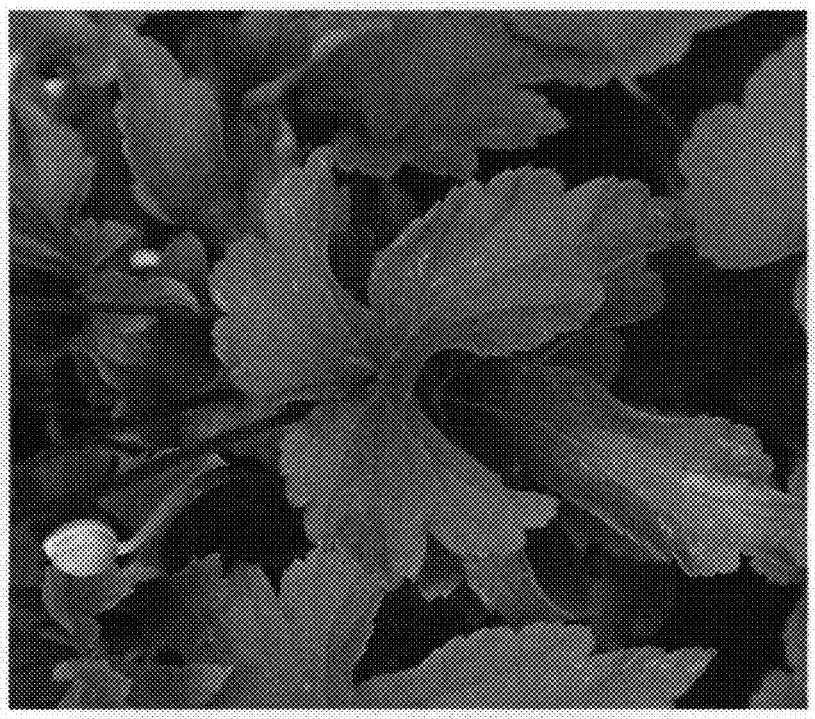
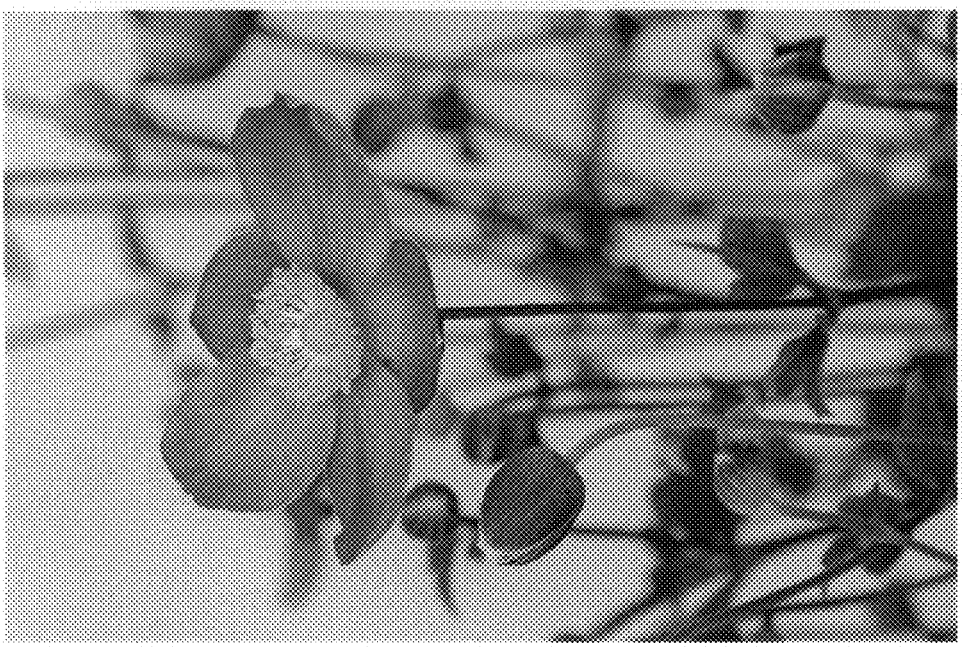

* * * * *